United States Patent [19]

Nakano et al.

[11] Patent Number: 4,847,387
[45] Date of Patent: Jul. 11, 1989

[54] ANTIBIOTIC COMPOUNDS DC-92B AND DC-92D

[75] Inventors: Hirofumi Nakano; Isami Takahashi; Fusao Tomita, all of Machida; Kozo Asano, Tsukuba; Toru Yasuzawa, Machida; Tadashi Ashizawa, Numazu; Keiichi Takahashi, Susono, all of Japan

[73] Assignee: Kyowa Hakko Kogyo Co., Ltd., Tokyo, Japan

[21] Appl. No.: 199,043

[22] PCT Filed: Jul. 17, 1987

[86] PCT No.: PCT/JP87/00524
§ 371 Date: Mar. 17, 1988
§ 102(e) Date: Mar. 17, 1988

[87] PCT Pub. No.: WO88/00591
PCT Pub. Date: Jan. 28, 1988

[30] Foreign Application Priority Data

Jul. 21, 1986 [JP] Japan ................. 61-171403

[51] Int. Cl.$^4$ .......................... C07D 311/78
[52] U.S. Cl. ................................. 549/384
[58] Field of Search ......................... 549/384

[56] References Cited

U.S. PATENT DOCUMENTS 3,334,016  8/1967  Schmitz ................. 167/65

FOREIGN PATENT DOCUMENTS 274693  12/1986  Japan .

OTHER PUBLICATIONS

Tetrahedron Letters, vol. 26, No. 27 (1985), Kawai et al., pp. 3273-3276.
Tetrahedron Letters, vol. 34, No. 24 (1978), Sequin et al., pp. 3623-3629.
CRC Handbook of Antibiotic Compounds, vol. 3 (1981), pp. 167, 9172-9173.

Primary Examiner—Nicky Chan
Attorney, Agent, or Firm—Fitzpatrick, Cella, Harper & Scinto

[57] ABSTRACT

The present invention relates to novel compounds DC-92B and DC-92D having anthraquinone moiety and represented by the following planar structural formula (I) and to a process for producing the same. These compounds can be produced by culture of a microorganism belonging to the genus Actinomadura, and are useful as medicaments because of their antibacterial and antitumor activities.

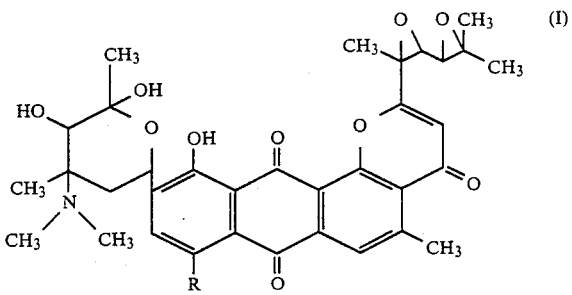

wherein R is a group represented by formula (II) or formula (III):

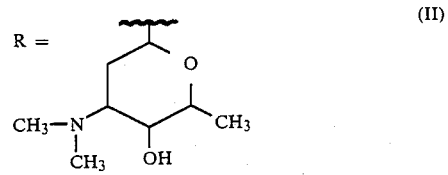

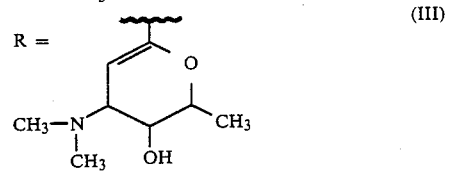

3 Claims, 6 Drawing Sheets

ANTIBIOTIC COMPOUNDS DC-92B AND DC-92D

TECHNICAL FIELD

The present invention relates to anti-tumor antibiotics DC-92B and DC-92D having the anthraquinone moiety and to a process for producing the same.

BACKGROUND ART

Mitomycins, anthracyclines, anthraquinones, etc. are known as anti-tumor antibiotics having the quinone moiety [CRC Handbook of Antibiotic Compounds, Volume 3, 1981 (CRC Press U.S.A.)]. Of these, the compounds represented by the following formula are illustrative of antraquinone compounds.

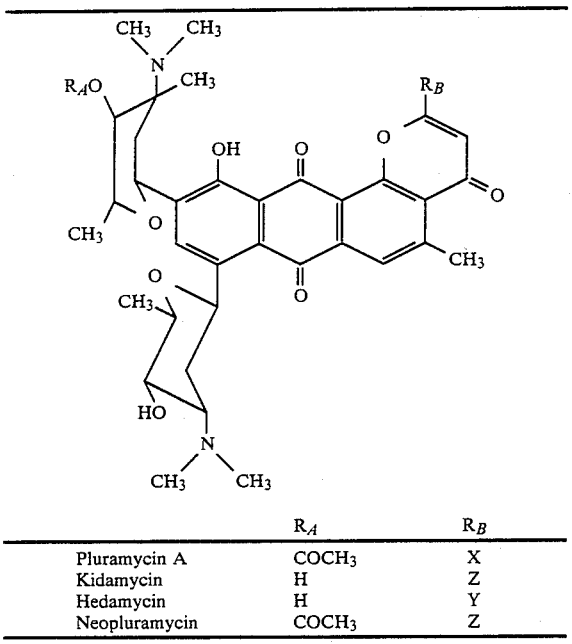

|  | $R_A$ | $R_B$ |
|---|---|---|
| Pluramycin A | $COCH_3$ | X |
| Kidamycin | H | Z |
| Hedamycin | H | Y |
| Neopluramycin | $COCH_3$ | Z |

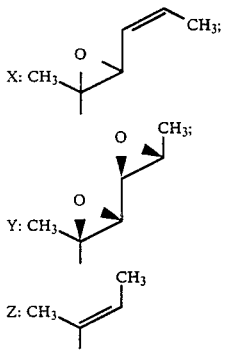

Mitomycin C, adriamycin, bleomycin and others are known as anti-tumor antibiotics used for chemotherapy against cancers. However, there has been a constant demand for substances with higher anti-tumor activity because these anti-tumor substances presently available are ineffective against some types of cancer and involve the problem of drug resistance.

DISCLOSURE OF THE INVENTION

In accordance with the present invention, novel substances DC-92B and/or DC-92D having anti-tumor and antibacterial activities can be obtained by culturing a microorganism belonging to the genus Actinomadura and capable of producing DC-92B and/or DC-92D.

The physicochemical properties of DC-92B are shown below.

(a) Molecular weight: 776 (Mass spectrometry; SI-MS m/z 777 $[M+H]^+$)

(b) Color: Dark red (c) Ultraviolet absorption spectra: As shown in FIGS. 1 and 2 [FIG. 1: in methanol, FIG. 2: in alkaline (NaOH) methanol]

(d) Infrared absorption spectrum: As shown in FIG. 5 (measured in $CHCl_3$)

(e) Solubility: Soluble in methanol, ethanol, acetone, chloroform, ethyl acetate, toluene and dimethylsulfoxide; sparingly soluble in water and hexane (f) $^1H$-NMR spectrum (400 MHz, measured in $CDCl_3$, internal standard: TMS) $\delta$(ppm): 13.88 (1H, br s), ca.9.7 (1H, br), 8.34 (1H, br s), 8.04 (1H, d, J=0.6 Hz), 6.53 (1H, s), 5.50 (1H, br d, J=11.0 Hz), 5.45 (1H, br dd, J=10.2, 1.4 Hz), 3.56 (1H, dq, J=8.6, 6.0 Hz), 3.54 (1H, s), 3.22 (1H, br dd, J=9.8, 8.6 Hz), 3.17 (1H, d, J=4.9 Hz), 3.02 (3H, d, J=0.6 Hz), 2.86 (1H, ddd, J=13.2, 9.8, 3.4 Hz), 2.72 (1H, d, J=4.9 Hz), 2.61 (6H, br s), ca.2.6 (1H), 2.32 (6H, s), 2.19 (1H, m), 1.91 (3H, s), 1.59 (3H, s), 1.44 (3H, d, J=6.0 Hz), 1.38 (1H, br dd, J=11.1, 3.8 Hz), 1.35 (3H, s), 1.12 (3H, s), ca.1.1 (1H, m), 1.08 (3H, s)

(g) $^{13}C$-NMR spectrum (100 MHz measured in $CDCl_3$, internal standard: TMS) $\delta$(ppm): 187.8, 183.2, 178.3, 164.9, 159.3, 156.0, 150.0, 140.0, 138.8, 137.5, 132.6, 126.2, 126.1, 126.0, 119.1, 115.6, 110.9, 100.0, 79.0, 77.5, 75.2, 71.7, 67.3, 63.6, 62.9, 59.9, 59.0, 58.6, 58.2, 43.1, 41.0, 40.4, 28.5, 25.2, 24.2, 24.1, 19.9, 19.7, 18.8, 14.3

(h) Thin layer chromatography: $R_f$=0.54 [Chemically bonded silica gel thin layer (HPTLC plate Art 15647, E. Merck), developer: toluene/acetone (6:4 V/V)]

(i) Weakly basic substance

The physicochemical properties of DC-92D are shown below.

(a) Molecular weight: 774 (Mass spectrometry; SI-MS m/z 775 $[M+H]^+$)

(b) Color: Dark red (c) Ultraviolet absorption spectra: As shown in FIGS. 3 and 4 [FIG. 3: in methanol, FIG. 4: in alkaline (NaOH) methanol]

(d) Infrared absorption spectrum: As shown in FIG. 6 (measured in $CHCl_3$)

(e) Solubility: Soluble in methanol, ethanol, acetone, chloroform, ethyl acetate, toluene and dimethylsulfoxide; sparingly soluble in water and hexane (f) $^1H$-NMR spectrum (400 MHz, measured in $CDCl_3$, internal standard: TMS) $\delta$(ppm): 13.68 (1H, br), ca.9.65 (1H, br), 8.02 (1H, br s), 7.84 (1H, d, J=0.5 Hz), 6.54 (1H, s), 5.46 (1H, br d, J=11.0 Hz), 4.97 (1H, d, J=2.1 Hz), 4.33 (1H, dq, J=9.5, 6.3 Hz), 3.66 (1H, dd, J=9.5, 8.4 Hz), 3.49 (1H, dd, J=8.4, 2.1 Hz), 3.48 (1H, s), 3.17 (1H, d, J=5.0 Hz), 3.02 (3H, d, J=0.5 Hz), 2.74 (1H, d, J=5.0 Hz), ca.2.6 (1H), 2.60 (6H, br s), 2.42 (6H, s), 1.91 (3H, s), 1.55 (3H, s), 1.42 (3H, d, J=6.3 Hz), 1.34 (3H, s), 1.33 (1H, dd, J=14.7, 11.5 Hz), 1.11 (3H, s), 1.09 (3H, s)

(g) $^{13}C$-NMR spectrum (100 MHz, measured in $CDCl_3$, internal standard: TMS) $\delta$(ppm): 188.0, 181.0, 178.3, 164.9, 159.8, 156.5, 156.1, 150.3, 138.7, 137.3, 136.4, 129.4, 128.8, 126.1 (2), 119.0, 116.3, 111.0, 100.0, 95.5, 79.0, 76.7, 69.2, 66.1, 63.6, 62.6, 59.8, 59.0, 58.6, 58.2, 43.3, 41.0, 40.9, 25.2, 24.25, 24.16, 19.8, 19.7, 17.7, 14.4

(h) Thin layer chromatography: $R_f=0.20$ [Chemically bonded silica gel thin layer (HPTLC plate Art 15647, E. Merck), developer: toluene/acetone (6:4 V/V)]

(i) Weakly basic substance

Planar structural formulas of DC-92B and DC-92D were determined as shown below based on the physicochemical properties given above in items (a), (c), (d), (f), (g), etc.

Biological properties of DC-92B and DC-92D are shown below.

(A) Minimum Inhibitory Concentration Against Various Bacteria (MIC: μg/ml)

| Bacteria tested | DC-92B | DC-92D |
|---|---|---|
| *Staphylococcus aureus* ATCC 6538P | 0.04 | 1.5 |
| *Bacillus subtilis* No. 10707 | 0.15 | 3.0 |
| *Klebsiella pneumoniae* ATCC 10031 | 2.5 | 25 |
| *Escherichia coli* ATCC 26 | 10 | 100 |
| *Shigella sonnei* ATCC 9290 | 10 | 100 |
| *Salmonella typhosa* ATCC 9992 | 40 | 100 |

The antibacterial activity was evaluated by the agar dilution method using a medium (pH 7) prepared by dissolving 3 g of Bacto-Tryptone (Difco Laboratories), 3 g of meat extract, 1 g of yeast extract, 1 g of glucose and 16 g of agar in 1 liter of water.

(B) Acute Toxicity

The acute toxicity values ($LD_{50}$) of DC-92B and DC-92D were about 0.31 mg/kg and about 5.6 mg/kg, respectively, by intraperitoneal administration to mice.

(C) Anti-Tumor Activity (1) Therapeutic effect against Salcoma 180 tumor

Six male ddY-strain mice each having a weight of about 20 g were used for each group as test animals, and $5\times10^6$ cells of Sarcoma 180 ascites tumor were implanted subcutaneously into the animals at the axilla. 0.2 ml of phosphate buffered saline (hereinafter referred to as PBS) containing DC-92B or DC-92D at various concentrations was administered once intraperitoneally 24 hours after implantation. The composition of PBS was 0.8 g/dl NaCl, 0.02 g/dl KCl, 1.15 g/dl $Na_2HPO_4$ and 0.02 g/dl $KH_2PO_4$ (pH 7.2).

For comparison, 0.2 ml of PBS containing mitomycin C was intraperitoneally administered to a group of animals 24 hours after tumor implantation. The table below shows the average tumor volume ($mm^3$) and T/C (T: average tumor volume of the test groups, C: average tumor volume of the control group which received an intraperitoneal administration of 0.2 ml of PBS) ten days after implantation.

| Compound | Dose (mg/kg) | Average tumor volume (mm³) | T/C |
|---|---|---|---|
| DC-92B | 0.31 | 828.6 | 0.39 |
| DC-92D | 6.25 | 764.9 | 0.36 |
|  | 3.125 | 679.9 | 0.32 |
|  | 1.563 | 1444.8 | 0.68 |
| Mitomycin C | 6.0 | 743.8 | 0.35 |
| Control | — | 2124.7 | — |

(2) Therapeutic effect against lymphocytic leukemia P388 tumor

Five male CDF1 mice each having a weight of about 22 g were used for each group as test animals, and $1\times10^6$ cells of lymphocytic leukemia P388 tumor were implanted intraperitoneally into the test animals. 0.2 ml of PBS containing DC-92B or DC-92D was administered once intraperitoneally 24 hours after implantation.

For comparison, 0.2 ml of PBS containing mitomycin C was intraperitoneally administered to a group of animals 24 hours after tumor implantation. The table below shows the mean survival days after implantation and T/C (T: mean survival days for the test groups, C: mean survival days for the control group).

| Compound | Dose (mg/kg) | Survival days | Increased Life Span (T/C) |
|---|---|---|---|
| DC-92B | 0 (control) | 11.0 | — |
|  | 0.15 | 16.2 | 1.47 |
|  | 0.025* | 15.5 | 1.41 |
|  | 0.0125* | 15.5 | 1.41 |
| DC-92D | 3.13 | 7.6 | 0.69 |
|  | 1.56 | 12.7 | 1.15 |
|  | 0.78 | 12.9 | 1.17 |
|  | 0.39 | 11.4 | 1.04 |
|  | 0.75* | 17.4 | 1.58 |
| Mitomycin C | 6.0 | 17.9 | 1.63 |

*Continuous administration for five days

The process for producing DC-92B and DC-92D is described below.

DC-92B and/or DC-92D can be obtained by culturing a DC-92B and/or DC-92D-producing strain belonging to the genus Actinomadura in a nutrient medium until DC-92B and/or DC-92D are accumulated in the culture, and recovering DC-92B and/or DC-92D from the culture. Any strains of the genus Actinomadura capable of producing DC-92B and/or DC-92D may be used as the DC-92B and/or DC-92D-producing strains. Some mutant strains derived therefrom through artificial mutation means such as ultraviolet irradiation have been found to be capable of producing DC-92B and/or DC-92D. A typical example is DO-92 strain.

Microbiological properties of DO-92 strain are shown below.

(1) Morphology

Aerial mycelium: Branched but not fragmented

Substrate mycelium: Not fragmented

Spore: Spores in short flexuous chains develop at the end of simply branched aerial mycelium.
Surface of spore: Smooth
Shape and size of: Elliptical, about 0.6 × 1.1 μm spore
Motility of spore: No movement observed
Formation of screlotium and sporangium is not observed.

(2) Color
Aerial mycelium: Beige
Substrate mycelium: Beige to yellowish brown
Soluble pigment: Cream to yellowish brown
Melanin pigment: Not formed (3) Chemical properties
Steric configuration of diaminopimelic acid: meso type
Whole cell sugar: A trace of madulose is present.

(4) Cultural characteristics on various culture media
Cultural characteristics of DO-92 strain on various media observed after culturing at 28° C. for three weeks are shown in Table 1. Color was represented in accordance with Color Harmony Manual (Container Corporation of America). In Table 1, G represents growth, AM the degree of formation of aerial mycelia and their color, SM the color of substrate mycelia, and P the formation of soluble pigment and its color.

TABLE 1

| Medium | Cultural characteristics | |
|---|---|---|
| Sucrose-nitrate agar medium | G | Poor |
| | AM | Poor; pearl (2ba) |
| | SM | Natural (3dc) |
| | P | None |
| Glucose-asparagine agar medium | G | Moderate |
| | AM | Poor; biscuit (2ec) |
| | SM | Biscuit (2ec) |
| | P | None |
| Glycerine-asparagine agar medium | G | Poor to moderate |
| | AM | None |
| | SM | Light ivory (2ca) |
| | P | None |
| Starch agar medium | G | Poor |
| | AM | Poor; pearl (3ba) |
| | SM | Transparent |
| | P | Bamboo (2gc) |
| Tyrosine agar medium | G | Moderate |
| | AM | Poor; pearl (3ba) |
| | SM | Honey gold (2ic) |
| | P | Bamboo (2gc) |
| Nutrient agar medium | G | Moderate |
| | AM | None |
| | SM | Gold (21c) |
| | P | Light wheat (2ea) |
| Yeast extract-malt extract agar medium | G | Good |
| | AM | Abundant; pearl (2ba) |
| | SM | Gold (21c) |
| | P | Honey gold (2ic) |
| Oatmeal agar medium | G | Good |
| | AM | None |
| | SM | Bamboo (2gc) |
| | P | Bamboo (2gc |
| Peptone-yeast extract-iron agar medium | G | Moderate |
| | AM | None |
| | SM | Topaz (3ne) |
| | P | None |

(5) Physiological properties
Growth temperature range was determined after 2 days of culturing. The action on defatted milk and cellulose was observed after 1 month of culturing at 28° C. The other observations were made after 2 weeks of culturing at 28° C.
 Growth temperature range: 20° to 37° C.
 Optimum growth temperature range: 28° to 32° C.
 Liquefaction of gelatin: Negative
 Decomposition of cellulose: Negative
 Coagulation of defatted milk: Negative
 Peptonization of defatted milk: Positive
 Formation of melanin pigment: Negative (6) Assimilation of carbon sources

| Carbon source | Growth | Carbon source | Growth |
|---|---|---|---|
| D-Glucose | + | D-Fructose | + |
| L-Arabinose | ± | L-Rhamnose | + |
| D-Xylose | ± | Sucrose | ± |
| Inositol | ± | Raffinose | ± |
| D-Mannitol | ± | | |

(+: Good growth, ±: Very poor growth)

(7) Identification of DO-92 strain
DO-92 strain belongs to the Type III cell wall group and to the Type B whole cell sugar group according to the classification of Lechevalier, et al. (Int. J. Syst. Bacteriol., 20, 435–443, 1970), since it contains mesodiaminopimelic acid in its cell walls, and madulose is detected as a characteristic sugar among whole cell sugars.

Morphological characteristics such as formation of aerial mycelia simply branched and formation of short spore chains at the end thereof indicate that this strain belongs to the genus Actinomadura in Actinomycetales. Therefore, DO-92 strain was identified as a strain of Actinomadura, named Actinomadura sp. DO-92, and deposited with the Fermentation Research Institute, Agency of Industrial Science and Technology under FERM BP-1019 on Apr. 23, 1986.

For the culturing in the present invention, conventional methods for culturing Actinomycetes are generally used. Any culture media may be employed which contain carbon sources, nitrogen sources, inorganic substances and other nutrients in proper amounts. As the carbon source, glucose, starch, glycerol, mannose, fructose, sucrose, molasses, etc. can be used either alone or in combination. Hydrocarbons, alcohols, organic acids, etc. may also be used depending upon the assimilability of the strain employed. As the nitrogen source, organic and inorganic nitrogen-containing compounds such as ammonium chloride, ammonium sulfate, ammonium nitrate, sodium nitrate and urea, and natural nitrogenous substances such as peptone, meat extract, yeast extract, dry yeast, corn steep liquor (CSL), soybean meal and Casamino acid can be used either alone or in combination. In addition, inorganic salts such as sodium chloride, potassium chloride, ferrous sulfate, zinc sulfate, manganese sulfate, copper sulfate, nickel sulfate, calcium carbonate and phosphates and added at need. Organic or inorganic substances which promote the production of DC-92B and/or DC-92D such as biotin and vitamins may also be added.

Culturing is preferably carried out by liquid culture, and most preferably by submerged stirring culture. Culturing temperature is 20° to 37° C., preferably 28° to 32° C. It is desirable to maintain the pH of the medium at 4 to 10, preferably 6 to 8 by adding aqueous ammonia or aqueous ammonium carbonate during the culturing. Usually, by liquid culture for 1 to 7 days, the desired substances are produced and accumulated in the culture. Culturing is discontinued when the amount of the products in the culture reaches the maximum.

For the isolation and purification of DC-92B and/or DC-92D from the culture, an ordinary method for isolating a microbial metabolite from the culture can be utilized. For example, the culture is subjected to filtration, centrifugation, or the like to remove microbial cells, and the resulting filtrate or supernatant is passed through a column packed with a non-ionic porous resin such as HP-20 (manufactured by Mitsubishi Chemical Industries Ltd.) to adsorb the active component. Then, the adsorbed active component is eluted with methanol. The eluate is concentrated to dryness, and the residue is extracted with ethyl acetate. The extract is again concentrated to dryness, and the residue is purified using gel filtering aids, silica gel (Wako Gel C-200; Wako Pure Chemical Industries, Ltd.), etc. to give a crude product of DC-92B and/or DC-92D. The product is further purified by treatment with silica gel (Wako Gel L.C. $NH_2$; Wako Pure Chemical Industries, Ltd.), etc. Purity of the obtained DC-92B and/or DC-92D can be further raised by recrystallization, HPLC and other purification techniques.

During the cultivation and purification steps, DC-92B and/or DC-92D can be traced by bioassay using *Bacillus subtilis* No. 10707, or by measuring ultraviolet absorption of thin layer chromatograms.

DC-92B and DC-92D can be used as anti-tumor agents in suitable dosage forms prepared by combination with at least one pharmaceutical diluent, adjuvant or carrier. For example, DC-92B and DC-92D are usually dissolved in physiological saline, glucose solution, lactose solution or mannitol solution to prepare injections and administered intravenously to mammals, particularly human beings, respectively in doses of 0.002–0.22 mg/kg and 0.04–4 mg/kg. They may also be administered intra-arterially, intraperitoneally or intrathoracically in similar doses. Freeze-drying according to the method specified in Pharmacopoeia of Japan may be applied to them, and injectable powder can be prepared by adding sodium chloride to freeze-dried DC-92B or DC-92D. The pharmaceutical preparations of these compounds may also contain pharmaceutically acceptable well-known diluents, adjuvants and/or carriers such as pharmaceutically acceptable salts. When the compounds are used as an injection, it is preferable, in some cases, to use an additive that enhances the solubility of the compounds. Doses may be adjusted appropriately depending on the age and conditions of patients. Administration schedule may also be adjusted depending on the dose, as well as the conditions of patients; intermittent administration, for example, once a week or once every three weeks, may be adopted. DC-92B and DC-92D may also be orally or rectally administered in similar doses and in the similar manner. They are used, with appropriate adjuvants, in the form of tablets, powder, granules or syrup for oral administration and in suppository form for rectal administration.

The anti-tumor agents thus prepared are expected to be useful for the therapy against chronic lymphocytic leukemia, chronic myeloid leukemia, breast cancer, stomach cancer, hepatoma, colon cancer, rectal carcinoma, lung cancer, pancreatic cancer, uterine carcinoma, cephalic and cervical tumors, etc. The suitable content of DC-92B or DC-92D in the above anti-tumor agents is 0.01 to 20 mg in 20 to 50 ml in the case of injection and 0.001 to 85 weight % when they are used in the form of tablets, capsules, powder, granules and suppositories.

EXAMPLE

Figure 1:
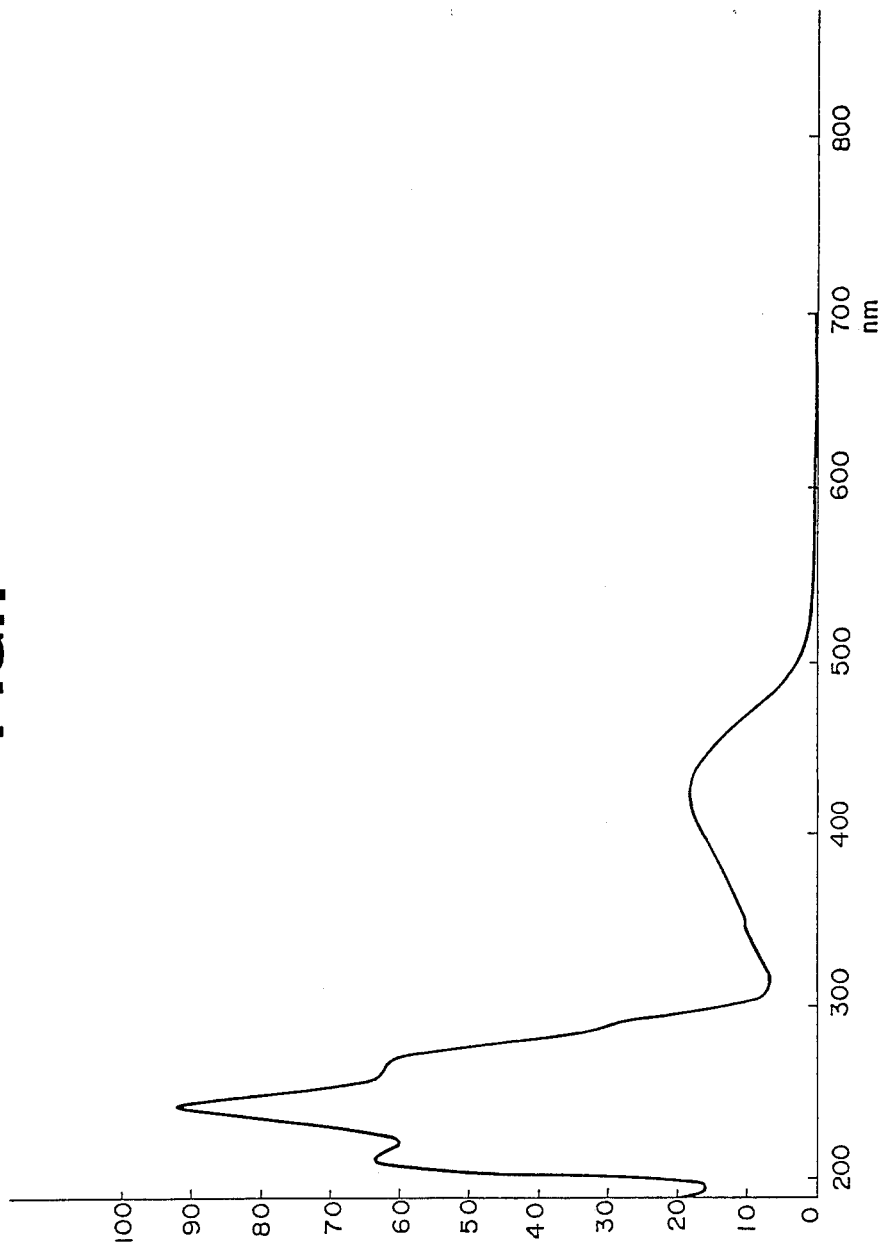
FIG. 1 shows the ultraviolet absorption spectrum of DC-92B in methanol.

An Example and Reference Examples of the present invention are shown below.

EXAMPLE

*Actinomadura* sp. DO-92 was used as the seed strain. The strain was inoculated into 10 ml of a seed medium (pH 7.2, prior to sterilization) containing 10 g/l soluble starch, 5 g/l Bacto-Tryptone (Difco Laboratories), 5 g/l yeast extract, 3 g/l, meat extract, 10 g/l glucose and 2 g/l calcium carbonate in a 50 ml-test tube, and incubated at 28° C. for 48 hours with shaking (200 rpm).

The seed culture thus obtained was inoculated into 300 ml of a medium having the same composition as above in a 2 l-flask, and subjected to shaking culture at 28° C. for 24 hours. The resulting seed culture was then inoculated into 15 l of a fermentation medium having the following composition in a 30 l-jar fermentor, and cultured with agitation and aeration (rotation: 250 rpm, aeration: 15 l/min.) at 28° C. Composition of the fermentation medium: 15 g/l glucose, 20 g/l cottonseed meal, 0.5 g/l $KH_2PO_4$ and 0.5 g/l $MgSO_4 \cdot 7H_2O$ (pH 7.0; adjusted with NaOH prior to sterilization)

Culturing was carried out for 90 hours, during which the pH of the medium was adjusted to 6.5–7.5 with aqueous ammonia. The microbial cells were separated from the culture by filtration, and the obtained filtrate (15 l) was passed through a column packed with 2 l of a non-ionic porous resin (HP-20; Mitsubishi Chemical Industries Ltd.) to adsorb the active components. The column was washed with water and then with 50% methanol to remove impurities. Elution was carried out with methanol, and the eluate was concentrated, adjusted to pH 10 and extracted with ethyl acetate. The ethyl acetate layer was concentrated, and the concentrate was passed through a column of a molecular sieve, Sephadex LH20 (Pharmacia Fine Chemicals Inc.), followed by elution with methanol to obtain active fractions. The active fractions were then subjected to column chromatography using chemically bonded silica gel (aminopropylsilane-bonded silica gel 40 μm; Baker Inc., USA). Elution was carried out with a 7:3 mixture of toluene and acetone to obtain crude products of DC-92B and DC-92D. The products were subjected to column chromatography using chemically modified silica gel (Wako Gel L.C $NH_2$; Wako Pure Chemical Industries, Ltd.) and eluted with a 7:3 mixture of toluene and acetone. The active fractions were concentrated to dryness, whereby 15 mg of DC-92B and 7 mg of DC-92D were obtained. These compounds showed the physicochemical and biological properties described hereinbefore.

During the cultivation and purification steps, DC-92B and DC-92D were traced by bioassay using *Bacillus subtilis* No. 10707, and by measuring ultraviolet absorption of thin layer chromatograms.

REFERENCE EXAMPLE 1

(Injection)

DC-92B (4 g) was dissolved in 20 l of ethanol, and the solution was filtered under pressure through a Millipore Filter (pore size: 0.22μ) for sterilization. The germ-free filtrate thus obtained was put in brown-colored vials (5.0 ml in each), and freeze-dried by a conventional method to obtain freeze-dried injectable powder (0.2 mg/vial).

REFERENCE EXAMPLE 2

(Tablets)

Tablets were prepared by a conventional method, each tablet consisting of 130 mg of DC-92D, 90 mg of lactose, 40 mg of corn starch, 4 mg of polyvinyl alcohol, 28 mg of Avicel and 1 mg of magnesium stearate.

What is claimed is:

1. A compound represented by the following planar structural formula (I):

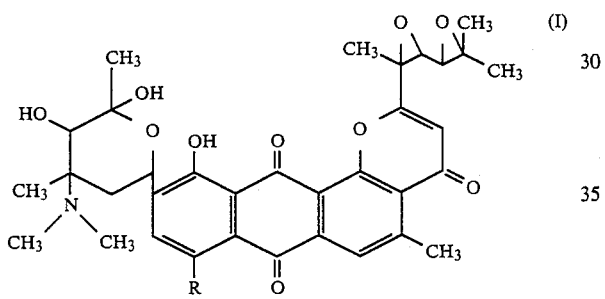

wherein R is a group represented by formula (II) or formula (III):

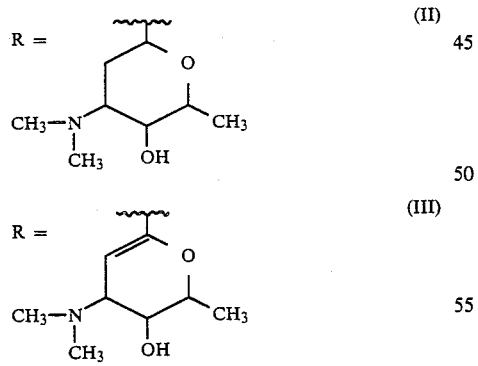

compound of formula (I) being called DC-92B when R is a group represented by formula (II), and called DC-92D when R is a group represented by formula (III).

Figure 2:
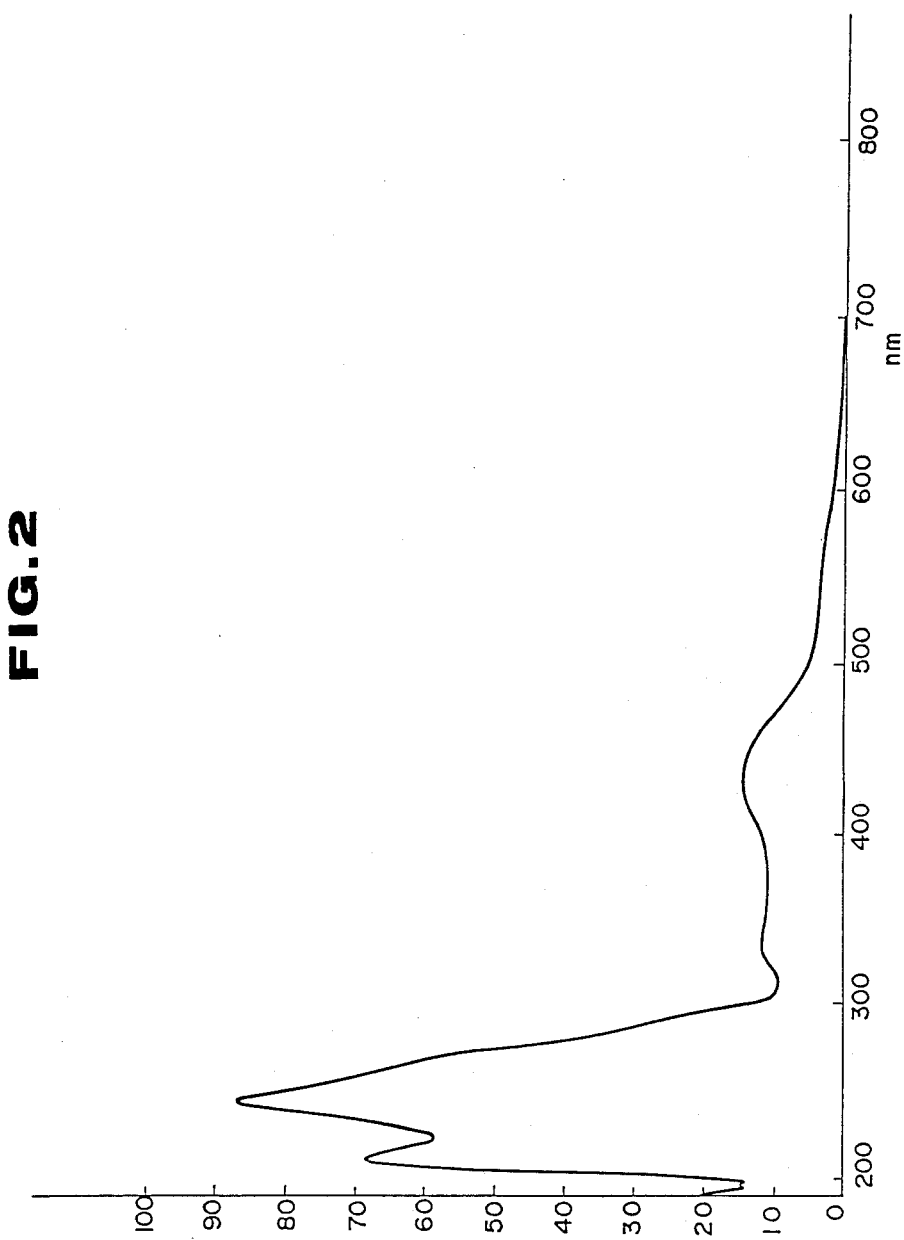
FIG. 2 shows the ultraviolet absorption spectrum of DC-92B in alkaline (sodium hydroxide) methanol.
Figure 5:
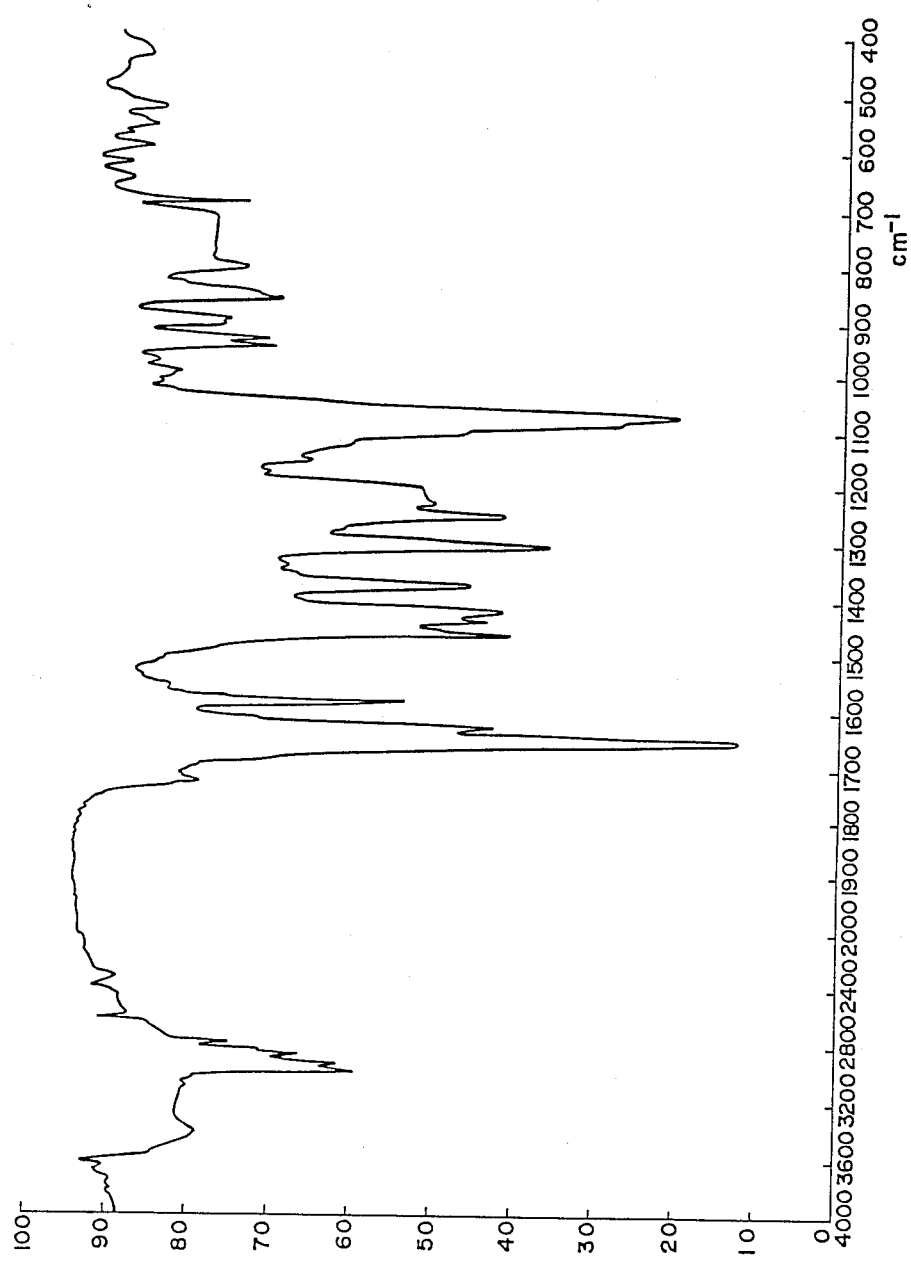
FIG. 5 shows the infrared absorption spectrum of DC-92B (measured in $CHCl_3$).

2. A compound according to claim 1, which is substance DC-92B characterized by the following physicochemical properties:

(a) Molecular weight: 776 (Mass spectrometry; SI-MS m/z 777 $[M+H]^+$)
(b) Color: Dark red
(c) Ultraviolet absorption spectra: As shown in FIGS. 1 and 2 [FIG. 1: in methanol, FIG. 2: in alkaline (NaOH) methanol]
(d) Infrared absorption spectrum: As shown in FIG. 5 (measured in $CHCl_3$)
(e) Solubility: Soluble in methanol, ethanol, acetone, chloroform, ethyl acetate, toluene and dimethylsulfoxide; sparingly soluble in water and hexane
(f) $^1H$-NMR spectrum (400 MHz, measured in $CDCl_3$, internal standard: TMS) δ(ppm): 13.88 (1H, br s), ca.9.7 (1H, br), 8.34 (1H, br s), 8.04 (1H, d, J=0.6 Hz), 6.53 (1H, s), 5.50 (1H, br d, J=11.0 Hz), 5.45 (1H, br dd, J=10.2, 1.4 Hz), 3.56 (1H, dq, J=8.6, 6.0 Hz), 3.54 (1H, s), 3.22 (1H, br dd, J=9.8, 8.6 Hz), 3.17 (1H, d, J=4.9 Hz), 3.02 (3H, d, J=0.6 Hz), 2.86 (1H, ddd, J=13.2, 9.8, 3.4 Hz), 2.72 (1H, d, J=4.9 Hz), 2.6, (6H, br s), ca.2.6 (1H), 2.32 (6H, s), 2.19 (1H, m), 1.91 (3H, s), 1.59 (3H, s), 1.44 (3H, d, J=6.0 Hz), 1.38 (1H, br dd, J=11.1, 3.8 Hz), 1.35 (3H, s), 1.12 (3H, s), ca.1.1 (1H, m), 1.08 (3H, s)

(g) $^{13}C$-NMR spectrum (100 MHz, measured in $CDCl_3$, internal standard: TMS) δ(ppm): 187.8, 183.2, 178.3, 164.9, 159.3, 156.0, 150.0, 140.0, 138.8, 137.5, 132.6, 126.2, 126.1, 126.0, 119.1, 115.6, 110.9, 100.0, 79.0, 77.5, 75.2, 71.7, 67.3, 63.6, 62.9, 59.9, 59.0, 58.6, 58.2, 43.1, 41.0, 40.4, 28.5, 25.2, 24.2, 24.1, 19.9, 19.7, 18.8, 14.3.

Figure 3:
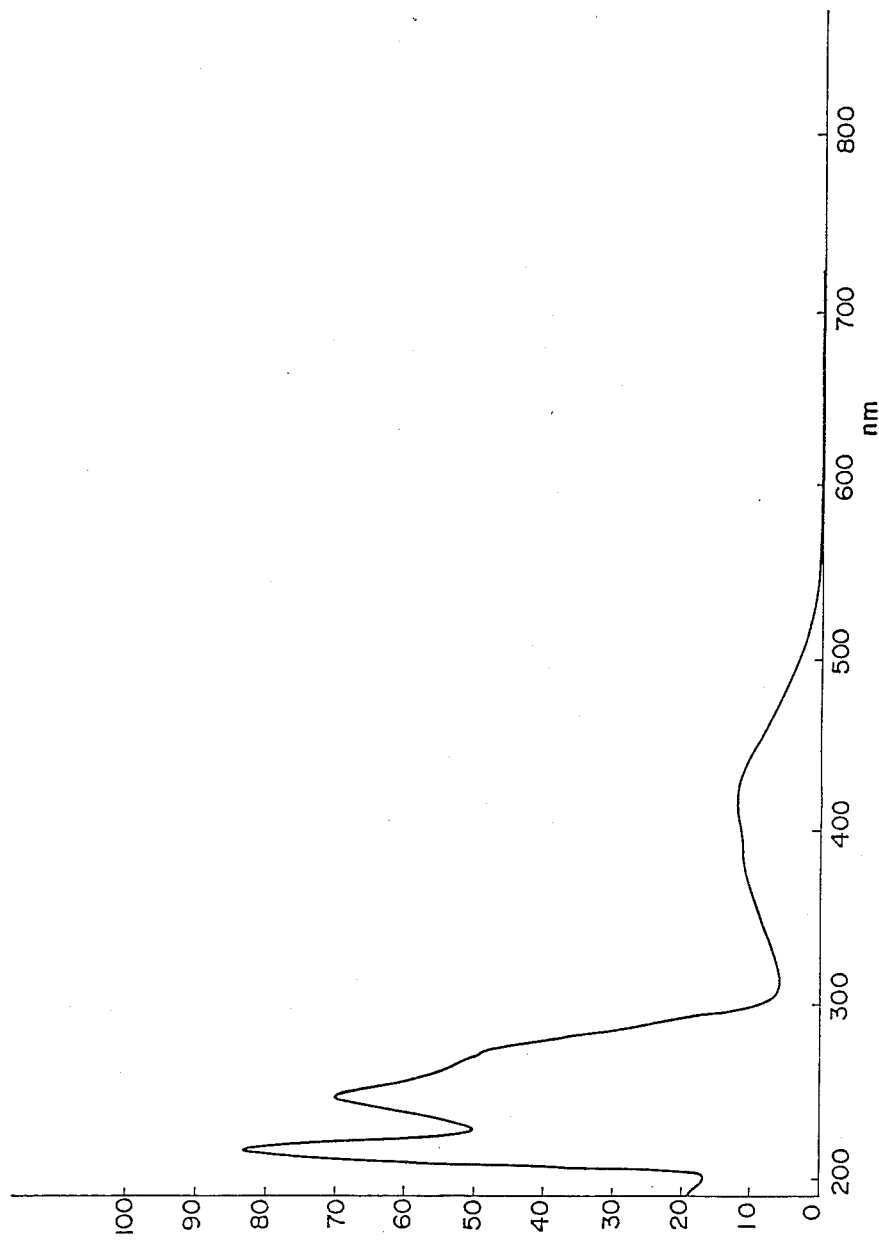
FIG. 3 shows the ultraviolet absorption spectrum of DC-92D in methanol.
Figure 4:
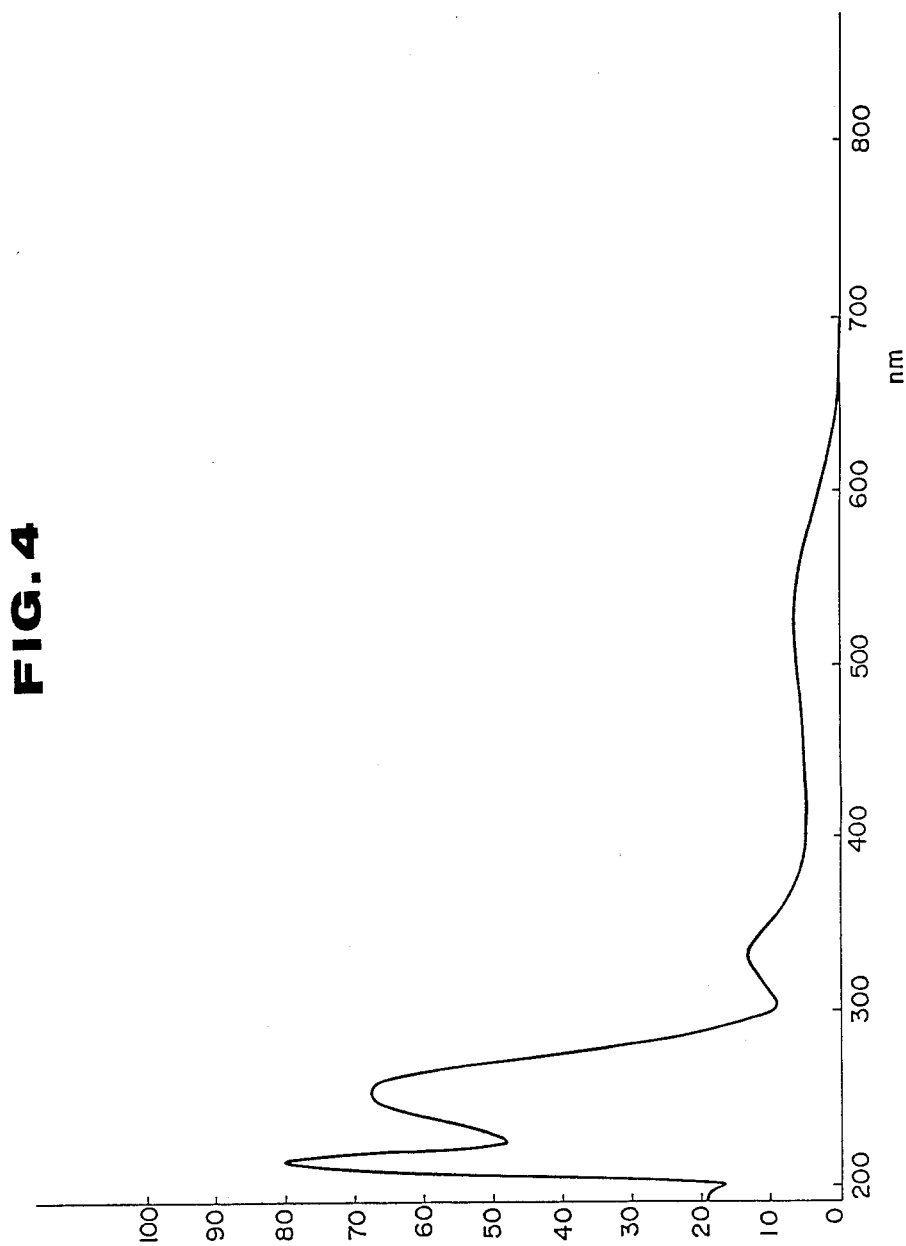
FIG. 4 shows the ultraviolet absorption spectrum of DC-92D in alkaline (sodium hydroxide) methanol.
Figure 6:
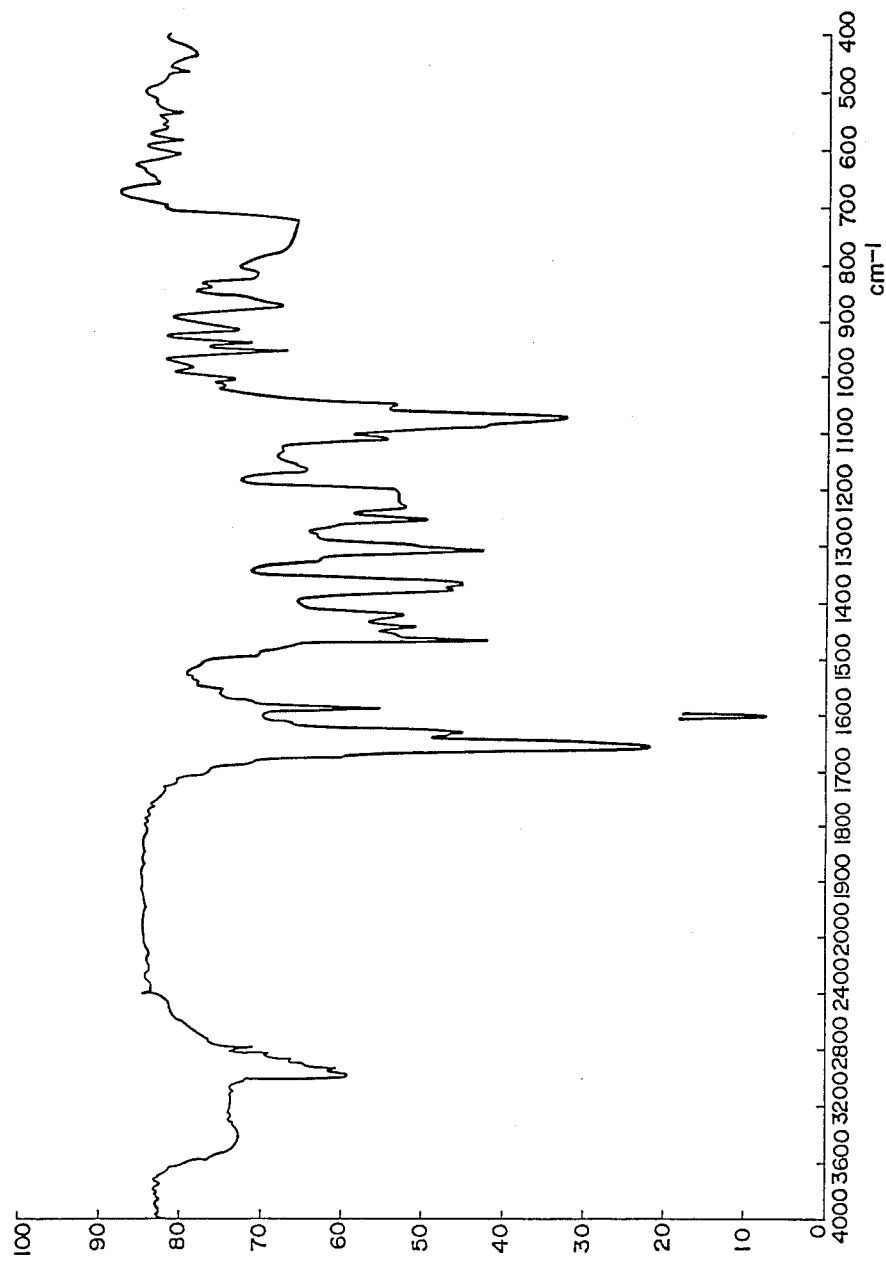
FIG. 6 shows the infrared absorption spectrum of DC-92D (measured in $CHCl_3$).

3. A compound according to claim 1, which is substance DC-92D characterized by the following physicochemical properties:

(a) Molecular weight: 774 (Mass spectrometry; SI-MS m/z 775 $[M+H]^+$)
(b) Color: Dark red
(c) Ultraviolet absorption spectra: As shown in FIGS. 3 and 4 [FIG. 3: in methanol, FIG. 4: in alkaline (NaOH) methanol]
(d) Infrared absorption spectrum: As shown in FIG. 6 (measured in $CHCl_3$)
(e) Solubility: Soluble in methanol, ethanol, acetone, chloroform, ethyl acetate, toluene and dimethylsulfoxide; sparingly soluble in water and hexane
(f) $^1H$-NMR spectrum (400 MHz, measured in $CDCl_3$, internal standard: TMS) δ(ppm): 13.68 (1H, br), ca.9.65 (1H, br), 8.02 (1H, br s), 7.84 (1H, d, J=0.5 Hz), 6.54 (1H, s), 5.46 (1H, br d, J=11.0 Hz), 4.97 (1H, d, J=2.1 Hz), 4.33 (1H, dq, J=9.5, 6.3 Hz), 3.66 (1H, dd, J=9.5, 8.4 Hz), 3.49 (1H, dd, J=8.4, 2.1 Hz), 3.48 (1H, s), 3.17 (1H, d, J=5.0 Hz), 3.02 (3H, d, J=0.5 Hz), 2.74 (1H, d, J=5.0 Hz), ca.2.6 (1H), 2.60 (6H, br s), 2.42 (6H, s), 1.91 (3H, s), 1.55 (3H, s), 1.42 (3H, d, J=6.3 Hz), 1.34 (3H, s), 1.33 (1H, dd, J=14.7, 11.5 Hz), 1.11 (3H, s), 1.09 (3H, S)

(g) $^{13}C$-NMR spectrum (100 MHz, measured in $CDCl_3$, internal standard: TMS) δ(ppm): 188.0, 181.0, 178.3, 164.9, 159.8, 156.5, 156.1, 150.3, 138.7, 137.3, 136.4, 129.4, 128.8, 126.1 (2), 119.0, 116.3, 111.0, 100.0, 95.5, 79.0, 76.7, 69.2, 66.1, 63.6, 62.6, 59.8, 59.0, 58.6, 58.2, 43.3, 41.0, 40.9, 25.2, 24.25, 24.16, 19.8, 19.7, 17.7, 14.4.

* * * * *

UNITED STATES PATENT AND TRADEMARK OFFICE
CERTIFICATE OF CORRECTION

PATENT NO. : 4,847,387
DATED : July 11, 1989
INVENTOR(S) : HIROFUMI NAKANO, ET AL.

It is certified that error appears in the above-identified patent and that said Letters Patent is hereby corrected as shown below:

COLUMN 1

Line 15, "antraquinone" should read --anthraquinone--.

COLUMN 5

Line 4, "of:" should read --of spore:-- and "spore" should be deleted.

COLUMN 10

Line 19, "2.6, (6H, br s)," should read --2.61 (6H, br s),--.

Signed and Sealed this

Tenth Day of April, 1990

Attest:

HARRY F. MANBECK, JR.

*Attesting Officer*      *Commissioner of Patents and Trademarks*